(12) United States Patent
Mohr et al.

(10) Patent No.: US 6,658,089 B1
(45) Date of Patent: Dec. 2, 2003

(54) SYSTEM AND METHOD FOR IMAGE IDENTIFICATION AND QUALITY INDICATION FOR RADIOGRAPHIC INSPECTION

(75) Inventors: Gregory Alan Mohr, Scotia, NY (US); Elizabeth Lokenberg Dixon, Delanson, NY (US); Michael Robert Hopple, Schenectady, NY (US); August David Matula, Sloansville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/064,417

(22) Filed: Jul. 11, 2002

(51) Int. Cl.[7] ............................................. H05G 1/28
(52) U.S. Cl. ...................................... 378/162; 378/163
(58) Field of Search ................................ 378/162, 163, 378/164, 58, 59, 62

(56) References Cited

U.S. PATENT DOCUMENTS

| | | | | |
|---|---|---|---|---|
| 3,952,194 A | * | 4/1976 | Bayonnet ..................... | 378/61 |
| 5,210,783 A | | 5/1993 | Wallace ....................... | 378/207 |
| 5,835,563 A | * | 11/1998 | Navab et al. ................ | 378/207 |
| 5,864,601 A | | 1/1999 | Cattorini et al. ............. | 378/59 |
| 6,041,094 A | * | 3/2000 | Russell ........................ | 378/37 |
| 6,317,482 B1 | | 11/2001 | Stefko ......................... | 378/56 |
| 6,333,970 B1 | * | 12/2001 | LeMaitre et al. ........... | 378/162 |

* cited by examiner

*Primary Examiner*—Louis Arana
(74) *Attorney, Agent, or Firm*—Penny A. Clarke; Patrick K. Patnode

(57) ABSTRACT

An image identification and quality indication system for radiographic inspection includes a flexible substrate, for positioning on a surface of an object to be inspected, and a number of locators and image quality indicators arranged on the flexible substrate. Each locator is configured for indicating a position on the object's surface in a respective radiographic image (image). Each image quality indicator is configured to indicate an image quality of the respective image. An image identification and quality indication method for radiographic inspection includes positioning the flexible substrate on the object's surface, including aligning the locators with a number of visible features on object's surface. The method further includes forming at least one reference mark and image quality mark in each of a number of images of the object, using a locator and image quality indicator, respectively. Each reference mark correlates the respective image with a position on the object.

34 Claims, 4 Drawing Sheets

SYSTEM AND METHOD FOR IMAGE IDENTIFICATION AND QUALITY INDICATION FOR RADIOGRAPHIC INSPECTION

BACKGROUND OF INVENTION

The invention relates generally to digital imaging, such as digital radiography, and more particularly to image identification and quality indication for imaging.

High-speed digital radiography for inspection of large objects, such as aircraft fuselage frames, requires quick acquisition of several thousand images. Because of the large size of the objects under inspection, accurate correlation of each image with its position on the object is desirable, to differentiate the image from other images which are similar in appearance. This referencing of each image to its respective position on the object is desirable for locating defects in the object, using the images.

In addition to image identification for accurate location of defects within the object undergoing inspection, it would be desirable to simultaneously determine the quality of the images. It would further be desirable for the image identification and quality indication to facilitate automated determination and recording of the image quality and location.

SUMMARY OF INVENTION

Briefly, in accordance with one embodiment of the present invention, an image identification and quality indication system for radiographic inspection is disclosed. The image identification and quality indication system includes a flexible substrate, for positioning on a surface of an object to be inspected, and a number of locators arranged on the flexible substrate. Each locator is configured for indicating at least one position on the surface of the object in a respective one of a number of radiographic images. The image identification and quality indication system further includes a number of image quality indicators arranged on the flexible substrate. Each image quality indicator is configured to indicate an image quality of the respective radiographic image.

An imaging system embodiment is also disclosed. The imaging system includes an x-ray source and a digital x-ray detector positioned with the object to be inspected disposed between the digital x-ray detector and the x-ray source. The digital x-ray detector is configured to be movable on a path along the object and to obtain a number of digital images of the object along the path. The inspection system further includes the flexible substrate, for positioning on a surface of the object to be inspected, and a number of locators and image quality indicators arranged on the flexible substrate.

An image identification and quality indication method embodiment, for radiographic inspection, is also disclosed. The image identification and quality indication method includes positioning the flexible substrate on a surface of the object to be inspected. The positioning includes aligning a number of locators on the flexible substrate with a number of visible features on the surface of the object. The method further includes forming at least one reference mark in each of a number of radiographic images of the object, using a respective locator. Each reference mark is adapted to correlate the respective radiographic image with a respective position on the object. The method further includes forming at least one image quality mark in each radiographic image, using a respective image quality indicator arranged on the flexible substrate.

An inspection method embodiment is also disclosed. The inspection method includes positioning the flexible substrate on a surface of the object to be inspected, including aligning a number of locators on the flexible substrate with a number of visible features on the surface of the object. The inspection method further includes imaging a portion of the object. The imaging includes activating the x-ray source and collecting an image with the digital x-ray detector. The imaging further includes forming at least one reference mark in the image using a respective locator, each of the reference marks being adapted to correlate the image with a respective position on the object. The imaging further includes forming at least one image quality mark in the image using a respective image quality indicator arranged on the flexible substrate. The inspection method further includes moving the digital x-ray detector to a subsequent detector position. The moving of the digital x-ray detector and the imaging steps are repeated for a number of detector positions to obtain a number of images of the object.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
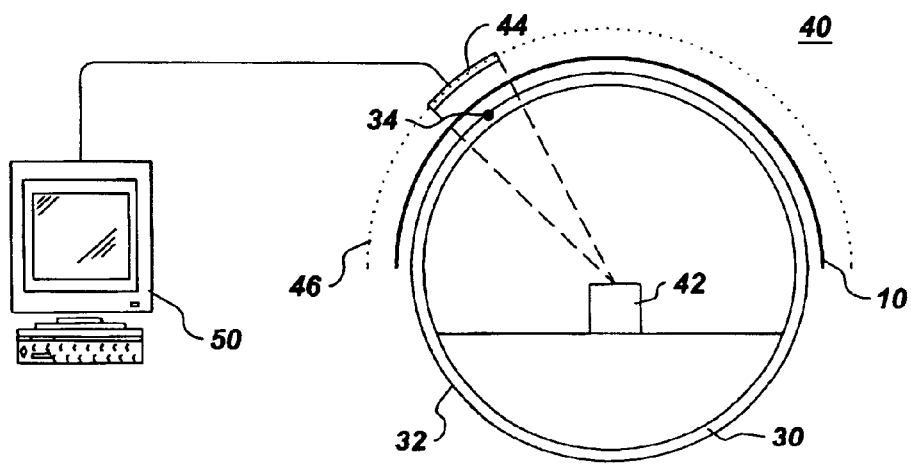
FIG. 1 illustrates an imaging system embodiment of the invention, which is exemplarily configured for imaging an aircraft fuselage.
Figure 2:
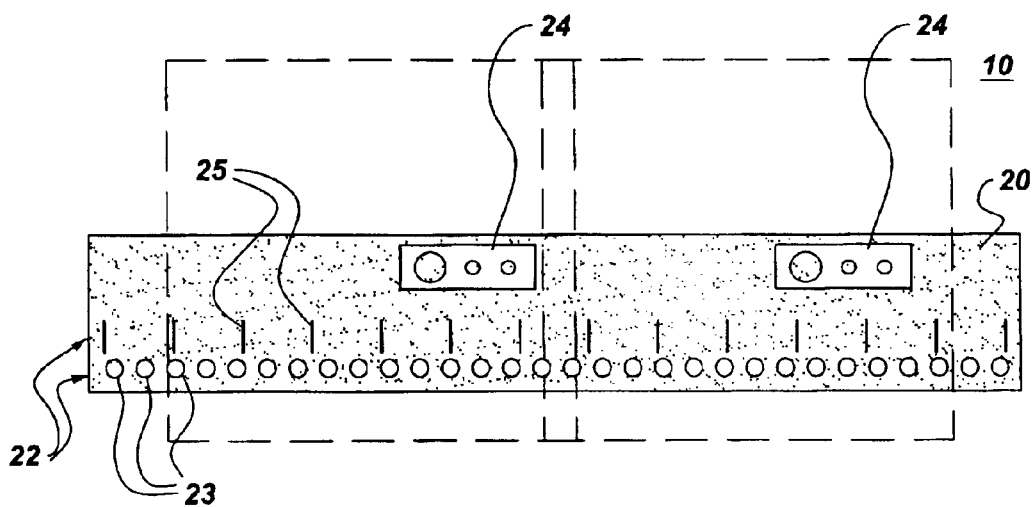
FIG. 2 illustrates an image identification and quality indication system embodiment of the invention.

An image identification and quality indication system 10 for radiographic inspection is described with reference to FIGS. 1, 2 and 5. The image identification and quality indication system 10 includes a flexible substrate 20 for positioning on a surface 32 of an object 30 to be inspected, as indicated for example in FIG. 1. Although the object 30 shown in FIG. 1 is an aircraft fuselage 30, image identification and quality indication system 10 is also applicable for inspection of other structures, such as aircraft wings, fuel tanks, boilers, fan blades, and combustor cases, and is particularly desirable for inspection of large structures involving a number of images at different locations on the structure. As indicated in FIG. 2, image identification and quality indication system 10 further includes a number of locators 22 arranged on flexible substrate 20. Each locator 22 is configured for indicating at least one position 34 on the surface 32 of the object 30 in a respective one of a number of radiographic images 36. Radiographic images 36 are discussed below with respect to FIG. 3. Image identification and quality indication system 10 also includes a number of image quality indicators 24 arranged on flexible substrate 20. Each image quality indicator 24 is configured to indicate an image quality of the respective radiographic image 36. As used here, the phrase "arranged on" includes arrangements of locators 22 and image quality indicators 24 formed on top of, formed underneath, or embedded within flexible substrate 20. The phrase "configured to indicate an image quality" should be understood to mean configured to indicate the image quality of the image in the image itself.

Figure 5:
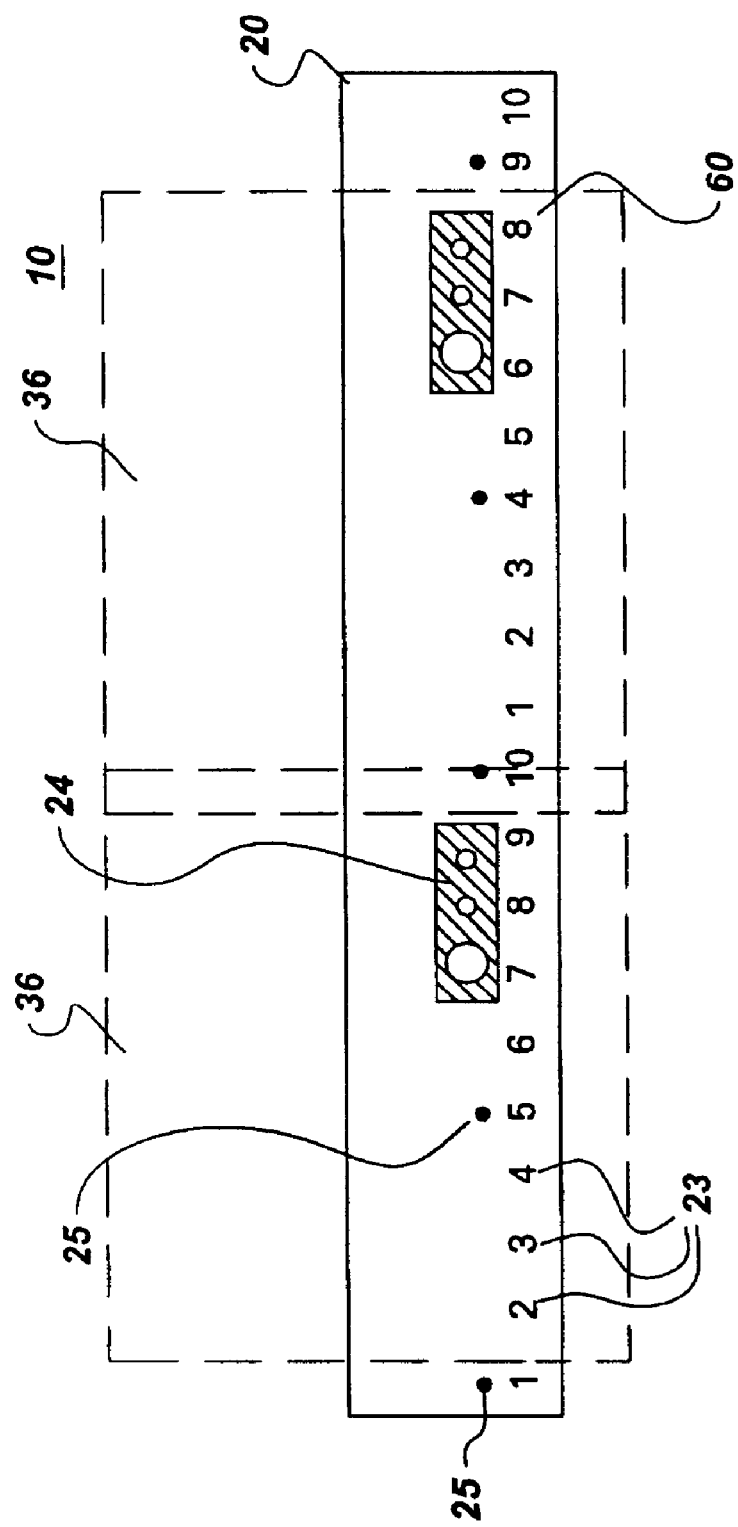
FIG. 5 illustrates another image identification and quality indication system embodiment of the invention.

For the particular embodiments illustrated in FIGS. 2 and 5, each locator 22 includes at least one visible marking 23 and at least one image locator 25. Visible markings 23 are configured to aid alignment of flexible substrate 20 with the object 30 to be imaged, and image locators 25 are opaque to x-ray radiation. Because they are opaque to x-rays, image locators 25 produce reference marks 37 in images 36, for correlating each of the images 36 with one or more respective positions 34 on object 30. Visible markings 23 are visible, for example to operators positioning flexible substrate 20 on surface 32. By "configured to aid alignment," it is meant that the visible markings 23 are arranged on flexible substrate 20 to correspond to visible features (not shown) on the object 30 to be inspected. Exemplary visible features for aircraft structures 30 include rivets and joints on an outer surface of the aircraft structure, and exemplary visible markings 23 are arranged on flexible substrate 20 for alignment with the visible markings. In this manner, image identification and quality indication system 10 can be repeatedly and consistently positioned on the surface 32 of the object 30 to be inspected.

According to a particular embodiment, flexible substrate 20 is substantially transparent to visible light and has a low x-ray attenuation. By "substantially transparent to visible light," it is meant that flexible substrate 20 transmits a sufficient portion of visible light to allow the operator to see through flexible substrate 20, such that the operator can see the visible features (not shown), of the object 30 to be inspected, through flexible substrate 20 for alignment with visible markings 23. By "low x-ray attenuation," it is meant that flexible substrate 20 transmits a sufficient fraction of incident x-rays that flexible substrate 20 does not interfere with x-ray imaging of the object 30, and more particularly is essentially invisible in x-ray image 36. Exemplary flexible substrates 20 comprise plastic, polyester films such as the polyester film sold under the trade name Mylar®, polyimide films such as the polyimide film sold under the trade name Kapton®, or woven materials such as cloth. An exemplary thickness for flexible substrate 20 is within a range of about ten to about 20 mils. However, the desired thickness of flexible substrate 20 varies with the material. Generally, the lower limit on the thickness is determined to reduce tearing, and the upper limit is constrained by weight, flexibility, and cost considerations.

Exemplary visible markings 23 are formed using ink and paint and are not visible in images 36 and examples include dots 23, as shown in FIG. 2, and characters, as shown in FIG. 5. Exemplary image locators 25 are formed of lead, tungsten, copper, or other materials that are opaque to x-rays. Other exemplary materials include ink or paint that is opaque to x-rays. In addition to the lines shown in FIG. 2, other exemplary image locators 25 comprise dots or a grid. According to a more particular embodiment, image locators 25 are situated outside the primary inspection area, to avoid obscuring the x-ray image 36 content. For example, image locators 25 are positioned on an edge 60 of x-ray image 36, as indicated in FIG. 5, for example.

According to a particular embodiment, each image quality indicator 24 is a penetrameter (also indicated by reference numeral 24), which is opaque to x-ray radiation. Penetrameters 24 are well known and hence will not be described in detail. Exemplary penetrameters 24 are formed of the same or a similar material as the object 30 to be inspected. The exemplary penetrameter 24 depicted in FIG. 2 comprises a sheet of metal, which corresponds to the metal forming object 30, having three holes of different diameters and/or thickness. Other exemplary penetrameters 24 comprise a number of steps of varying thickness (not shown) or sets-of wires of varying diameters (not shown). The type of penetrameter 24 selected depends upon the application requirements to demonstrate image quality. To secure image locators 25 and penetrameters 24 to flexible substrate 20, according to a more particular embodiment, flexible substrate 20 is laminated. By "laminated," it is meant that flexible substrate 20 is laminated on at least one side thereof.

Figure 3:
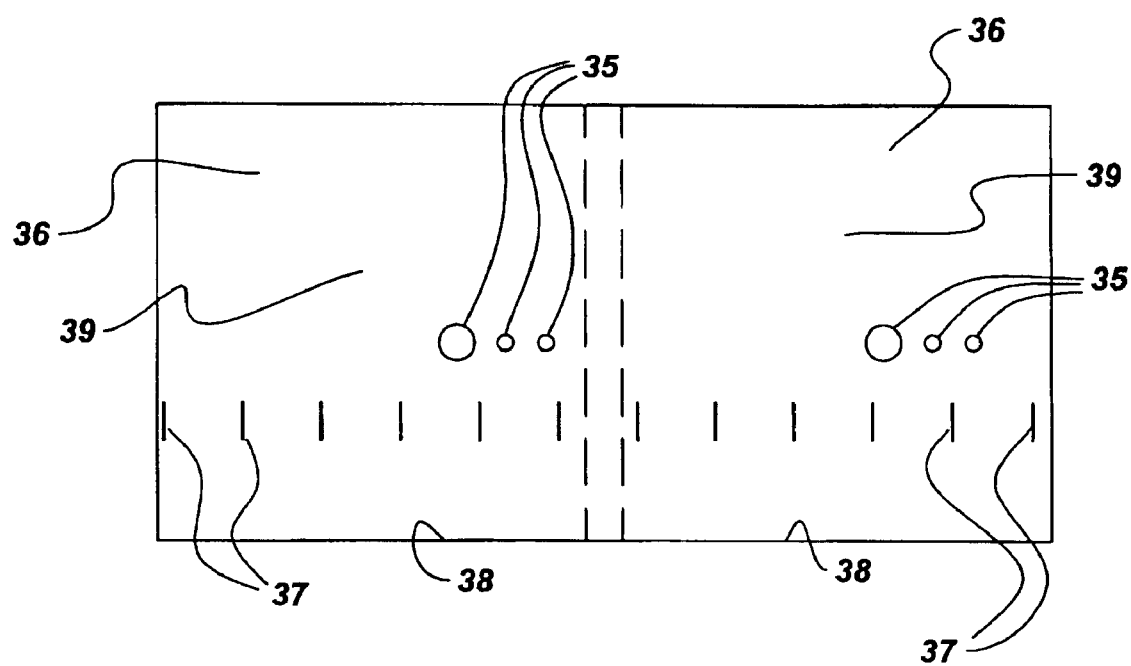
FIG. 3 depicts two neighboring, exemplary radiographic images.

To produce reference marks 37 and image quality marks 35 for each of the radiographic images 36 while facilitating a set of clear radiographic images 36 of object 30, according to a particular embodiment, each locator 22 and image quality indicator 24 is positioned on flexible substrate 20 to lie within a boundary 38 of the respective radiographic image 36 and outside a main portion 39 of the respective radiographic image. Two neighboring exemplary radiographic images 36 are depicted in FIG. 3. As schematically shown, reference marks 37 and image quality marks 35 are formed within image boundary 38 but outside the main portion 39 of the images 36. As reference and image quality marks 37, 35 are formed using image locators 25 and image quality indicators 24, these elements of image identification and quality indication system 10 are correspondingly positioned to lie within boundary 38 but outside main portion 39. It should be noted that although reference and image quality marks 37,35 are shown below main portion 39 of radiographic images 36, reference and image quality marks 37, 35 may also be above or to the side of the main portions 39 of radiographic images 36.

Figure 4:
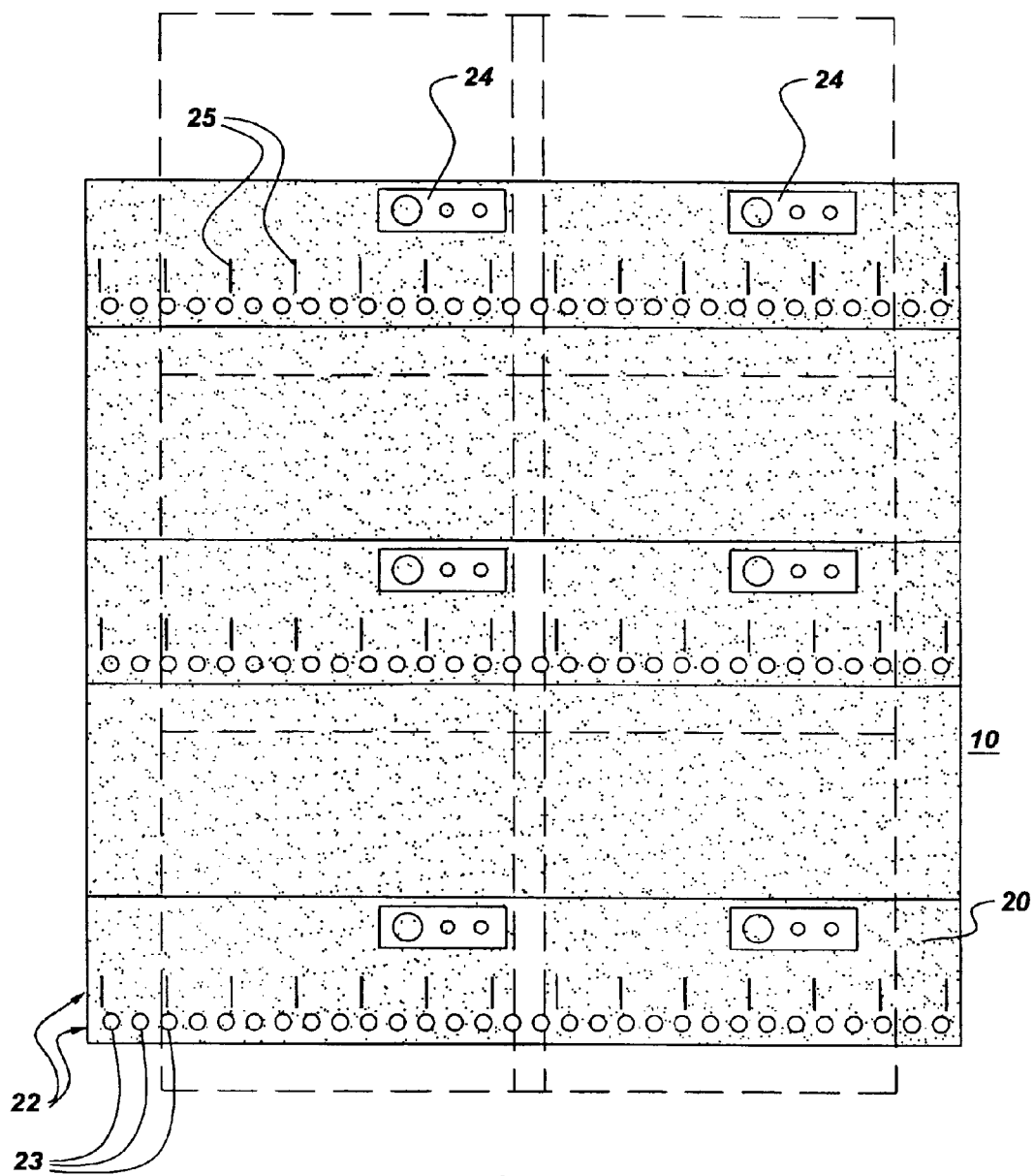
FIG. 4 shows a two dimensional array embodiment of the image identification and quality indication system.

In order to inspect a large area of a large object 30, for the embodiment shown in FIG. 4, locators 22 and image quality indicators 24 are arranged in a two dimensional array on flexible substrate 20. The number and length of the sets of locators 20 and image quality indicators 24 varies with the size and topology of the object 30 to be inspected. For the embodiment shown in FIG. 2, locators 22 and image quality indicators 24 are arranged in a linear array on flexible substrate 20.

An imaging system 40 embodiment is described with respect to FIGS. 1 and 2. As shown in FIG. 1, imaging system 40 includes an x-ray source 42 and a digital x-ray detector 44 positioned with the object 30 to be inspected disposed between digital x-ray detector 44 and x-ray source 42. As indicated in FIG. 1, digital x-ray detector 44 is configured to be movable on a path 46 along object 30 and to obtain a number of digital images 36 of the object 30 along the path 46. Imaging system 40 further includes a flexible substrate 20 for positioning on a surface 32 of object 30 and a number of locators 22 and image quality indicators 24 arranged on flexible substrate 20. Locators 22 and image quality indicators 24 are discussed above. Although the object 30 shown in FIG. 1 is an aircraft fuselage 30, imaging system 40 may be used to inspect a wide variety of objects 30, examples of which include aircraft wings, fuel tanks, boilers, fan blades, and combustor cases. Imaging system 40 is particularly desirable for inspection of large structures, such as aerospace and aircraft structures, large castings and welded fabrications, involving a number of images at different locations on the structure.

As discussed above with respect to image identification and quality indication system 10, according to a particular embodiment of imaging system 40, each locator 22 includes at least one visible marking 23 and at least one image locator 25, as shown for example in FIG. 2. Also as discussed above, according to a particular embodiment of imaging system 40, each locator 22 and image quality indicator 24 is positioned on flexible substrate 20 to lie within boundary 38 of the respective radiographic image 36 and outside main portion 39 of the respective radiographic image, as indicated for example in FIG. 3. According to particular embodiments of imaging system 40, locators 22 and image quality indicators 24 are arranged in a two dimensional or a linear array, as shown for example in FIGS. 4 and 2, respectively.

For the embodiment illustrated in FIG. 1, imaging system 40 further includes a computer 50, which is configured to process each of the digital images 36, to determine whether the image quality of each of the digital images satisfies a predetermined standard. Computer 50 is further configured to record the position 34 of each digital image 36 and whether the image quality of the respective digital image 36 is satisfactory or unsatisfactory. As used here, the phrase "configured to" means that the computer is equipped with a combination of hardware and software for processing the digital images 36 as described, as will be understood by those skilled in the art. It should be noted that the present invention is not limited to any particular computer for performing the processing tasks of the invention and that the term "computer" is used here to denote any machine capable of performing the calculations, or computations, necessary to perform the tasks of the invention.

According to a particular embodiment, computer 50 is further configured to apply optical character recognition to a number of reference marks 37 to determine the position 34 of each of the digital images 36. Exemplary reference marks 37 are illustrated in FIG. 3 and are formed in the digital images using locators 22, and more particularly using image locators 25. Beneficially, applying optical character recognition to reference marks 37 facilitates automatic recording by position 34 of the digital images 36 with acceptable image quality and of the digital images 36 that need to be retaken.

An image identification and quality indication method embodiment of the invention, for radiographic inspection, is described with respect to FIGS. 1–3. As indicated in FIG. 1, the image identification and quality indication method includes positioning flexible substrate 20 on a surface 32 of object 30. The positioning includes aligning a number of locators 22, and more particularly aligning a number of visible markings 23, on flexible substrate 20 with a number of visible features (not shown) on the surface 32 of object 30. For an aircraft fuselage 30, exemplary visible features include rivets and joints (not shown) on an outer surface 32 of aircraft fuselage 30. The image identification and quality indication method further includes forming at least one reference mark 37 in each of a number of radiographic images 36 of object 30, as indicated for example in FIG. 3. Each reference mark 37 is formed using a respective one of the locators 22, and, more particularly, a respective one of the image locators 25. Each reference mark 37 is adapted to correlate the respective radiographic image 36 with a respective position 34 on object 30. In this manner, the radiographic images 36 can be uniquely identified. The image identification and quality indication method further includes forming at least one image quality mark 35 in each radiographic image 36, using a respective image quality indicator 24, such as a penetrameter 24, which is arranged on flexible substrate 20. Formation of image quality marks 35 in radiographic images facilitates direct determination of the image quality of each of the radiographic images 36.

For the particular embodiment shown in FIG. 3, the reference and image quality marks 37, 35 are formed within a boundary 38 of the respective radiographic image 36 and outside a main portion 39 of the respective radiographic image. This facilitates image identification and quality indication for a set of clear radiographic images 36 of object 30.

Although the application of image identification and quality indication method shown in FIG. 1 is to an aircraft fuselage 30, the image identification and quality indication method is applicable to a variety of structures including aircraft wings, fuel tanks, boilers, fan blades, and combustor cases. Other desirable applications of image identification and quality indication method include large structures, such as aerospace and aircraft structures, large castings and welded fabrications, the inspection of which involves obtaining a number of images at different locations on the structure.

According to one embodiment, the image identification and quality indication method further includes visually inspecting each of the image quality marks 35 to determine whether the image quality of the respective radiographic image 36 is satisfactory. Although the image quality marks may be visually inspected, it is desirable to automate the inspection process, for both time and accuracy considerations. Accordingly, for the embodiment shown in FIG. 1, the image identification and quality indication method further includes inspecting each of the image quality marks 35 using computer 50 to determine whether the image quality of the respective radiographic image 36 satisfies a predetermined standard. The method further includes using computer 50 to record a position 34 of each of the radiographic images 36 and whether the image quality is satisfactory or unsatisfactory for each of the radiographic images 36. To determine the position 34 of each of the radiographic images 36, the image identification and quality indication method further includes applying optical character recognition to each of the reference marks 37, according to a more particular embodiment. Application of optical character recognition is performed using computer 50.

An inspection method embodiment of the invention is described with reference to FIGS. 1–3. As indicated in FIG. 1, the inspection method includes positioning flexible substrate 20 on a surface 32 of the object 30 to be inspected. The positioning includes aligning a number of locators 22 on flexible substrate 20 with a number of visible features on the surface 32 of object 30. The inspection method further includes imaging a portion of object 30. The imaging includes activating x-ray source 42 and collecting an image 36 with digital x-ray detector 44. The imaging further includes forming at least one reference mark 37 in the image 36 using a respective locator 22, each of the reference marks 37 being adapted to correlate the image 36 with a respective position 34 on object 30. The imaging further includes forming at least one image quality mark 35 in image 36, using a respective image quality indicator 24 arranged on flexible substrate 20. The inspection method further includes moving digital x-ray detector 44 to a subsequent detector position. The moving and imaging steps are repeated for a number of detector positions to obtain a number of images 36 of object 30. Reference and image quality marks 37, 35 are formed during imaging, for example, using image locators 25 and penetrameters 24, respectively, image locators 25 and penetrameters 24 being arranged on flexible substrate 20, as discussed above. According to a particular embodiment, the inspection method further includes inspecting the image quality marks 35, either visually or via computer 50, to determine whether the image quality of the respective image 36 is satisfactory.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An image identification and quality indication system for radiographic inspection, said system comprising:
   a flexible substrate for positioning on a surface of an object to be inspected;
   a plurality of locators arranged on said flexible substrate, each of said locators being configured for indicating at least one position on the surface of the object in a respective one of a plurality of radiographic images; and
   a plurality of image quality indicators arranged on said flexible substrate, each of said image quality indicators being configured to indicate an image quality of the respective radiographic image.

2. The image identification and quality indication system of claim 1, wherein each of said locators comprises at least one visible marking and at least one image locator, said visible marking being configured to aid alignment of said flexible substrate with the object to be imaged, and said image locator being opaque to x-ray radiation.

3. The image identification and quality indication system of claim 1, wherein each of said image quality indicators comprises a penetrameter, which is opaque to x-ray radiation.

4. The image identification and quality indication system of claim 3, wherein said flexible substrate is substantially transparent to visible light and has a low x-ray attenuation.

5. The image identification and quality indication system of claim 4, wherein said flexible substrate is laminated.

6. The image identification and quality indication system of claim 1, wherein each of said locators and image quality indicators is positioned on said flexible, substrate to lie within a boundary of the respective radiographic image and outside a main portion of the respective radiographic image.

7. The image identification and quality indication system of claim 1, wherein the object to be imaged comprises an aircraft fuselage.

8. The image identification and quality indication system of claim 1, wherein said locators and said image quality indicators are arranged in a two dimensional array on said flexible substrate.

9. The image identification and quality indication system of claim 1, wherein said locators and said image quality indicators are arranged in a linear array on said flexible substrate.

10. An imaging system comprising:
    an x-ray source;
    a digital x-ray detector positioned with an object to be inspected disposed between said digital x-ray detector and said x-ray source, said digital x-ray detector being configured to be movable on a path along the object and being configured to obtain a plurality of digital images of the object along the path;
    a flexible substrate for positioning on a surface of the object to be inspected;
    a plurality of locators arranged on said flexible substrate, each of said locators being configured for indicating at least one position on the surface of the object in a respective one of the digital images; and
    a plurality of image quality indicators arranged on said flexible substrate, each of said image quality indicators being configured to indicate an image quality of the respective digital image.

11. The imaging system of claim 10, wherein each of said locators comprises at least one visible marking and at least one image locator, said visible marking being configured to aid alignment of said flexible substrate with the object to be imaged, and said image locator being opaque to x-ray radiation.

12. The imaging system of claim 11, wherein each of said image quality indicators comprises a penetrameter, which is opaque to x-ray radiation, and wherein said flexible substrate is substantially transparent to visible light and has a low x-ray attenuation.

13. The imaging system of claim 12, wherein each of said locators and image quality indicators is positioned on said flexible substrate to lie within a boundary of the respective digital image and outside a main portion of the respective digital image.

14. The imaging system of claim 12, wherein the object to be imaged comprises an aircraft fuselage.

15. The imaging system of claim 12, wherein said locators and said image quality indicators are arranged in a two dimensional array on said flexible substrate.

16. The imaging system of claim 12, wherein said locators and said image quality indicators are arranged in a linear array on said flexible substrate.

17. The imaging system of claim 12 further comprising a computer, which is configured to process each of the digital images, to determine whether the image quality of each of the digital images satisfies a predetermined standard, and to record the position of each of the images and whether the image quality of the respective digital image is satisfactory or unsatisfactory.

18. The imaging system of claim 17, wherein said computer is further configured to apply optical character recognition to a plurality of reference marks to determine the position of each of the digital images, wherein the reference marks are formed in the digital images using said locators.

19. An image identification and quality indication method for radiographic inspection, said method comprising:
    positioning a flexible substrate on a surface of an object to be inspected, said
    positioning including aligning a plurality of locators on the flexible substrate with a plurality of visible features on the surface of the object;
    forming at least one reference mark in each of a plurality of radiographic images of the object, said formation of each of the reference marks comprising using a respective one of the locators, and each of the reference marks being adapted to correlate the respective radiographic image with a respective position on the object; and
    forming at least one image quality mark in each of the radiographic images, said formation of each of the image quality marks comprising using a respective one of a plurality of image quality indicators arranged on the flexible substrate.

20. The image identification and quality indication method of claim 19, wherein each of the locators comprises at least one visible marking and at least one image locator, the image locator being opaque to x-ray radiation, wherein said formation of each of the reference marks comprises using a respective one of the image locators, and wherein said positioning comprises aligning the visible markings with the visible features on the surface of the object.

21. The image identification and quality indication method of claim 20, wherein each of the image quality indicators comprises a penetrameter, which is opaque to x-ray radiation, and wherein the flexible substrate is substantially transparent to visible light and has a low x-ray attenuation.

22. The image identification and quality indication method of claim 21, wherein said formation steps comprise forming each of the reference and image quality marks within a boundary of the respective radiographic image and outside a main portion of the respective radiographic image.

23. The image identification and quality indication method of claim 21, wherein the object to be imaged comprises an aircraft fuselage.

24. The image identification and quality indication method of claim 21, further comprising visually inspecting each of the image quality marks to determine whether the image quality of the respective radiographic image is satisfactory.

25. The image identification and quality indication method of claim 21, further comprising:

inspecting each of the image quality marks using a computer to determine whether the image quality of the respective radiographic image satisfies a predetermined standard; and recording a position of each of the radiographic images and whether the image quality is satisfactory or unsatisfactory for each of the radiographic images, wherein said recording is performed using the computer.

26. The image identification and quality indication method of claim 25, further comprising applying optical character recognition to each of the reference marks to determine the position of each of the radiographic images, wherein said application of optical character recognition is performed using the computer.

27. An inspection method comprising:

positioning a flexible substrate on a surface of an object to be inspected, said positioning comprising aligning a plurality of locators on the flexible substrate with a plurality of visible features on the surface of the object;

imaging a portion of the object, said imaging comprising activating an x-ray source and collecting an image with a digital x-ray detector, said imaging further comprising:

forming at least one reference mark in the image using a respective one of the locators, each of the reference marks being adapted to correlate the image with a respective position on the object; and forming at least one image quality mark in the image using a respective one of a plurality of image quality indicators arranged on the flexible substrate; and moving the digital x-ray detector to a subsequent detector position, wherein said moving the digital x-ray detector and said imaging are repeated for a plurality of detector positions to obtain a plurality of images of the object.

28. The inspection method of claim 27, wherein each of the locators comprises at least one visible marking and at least one image locator, the image locator being opaque to x-ray radiation, wherein said formation of each of the reference marks comprises using a respective one of the image locators, and wherein said positioning comprises aligning the visible markings with the visible features on the surface of the object.

29. The inspection method of claim 28, wherein each of the image quality indicators comprises a penetrameter, which is opaque to x-ray radiation, and wherein the flexible substrate is substantially transparent to visible light and has a low x-ray attenuation.

30. The inspection method of claim 29, wherein said formation steps comprise forming each of the reference and image quality marks within a boundary of the respective image and outside a main portion of the respective image.

31. The inspection method of claim 29, wherein the object to be inspected comprises an aircraft fuselage.

32. The inspection method of claim 29, further comprising visually inspecting each of the image quality marks to determine whether the image quality of the respective image is satisfactory.

33. The inspection method of claim 29, further comprising:

inspecting each of the image quality marks using a computer to determine whether the image quality of the respective image satisfies a predetermined standard; and recording a position of each of the images and whether the image quality is satisfactory or unsatisfactory for each of the images, wherein said recording is performed using the computer.

34. The inspection method of claim 33, further comprising applying optical character recognition to each of the reference marks to determine the position of each of the images, wherein said application of optical character recognition is performed using the computer.

* * * * *